United States Patent
Unberath et al.

(10) Patent No.: US 12,268,533 B2
(45) Date of Patent: Apr. 8, 2025

(54) MACHINE LEARNING MODEL TO ADJUST C-ARM CONE-BEAM COMPUTED TOMOGRAPHY DEVICE TRAJECTORIES

(71) Applicant: The Johns Hopkins University, Baltimore, MD (US)

(72) Inventors: Mathias Unberath, Baltimore, MD (US); Jan-Nico Zaech, Zurich (CH)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 18/659,587

(22) Filed: May 9, 2024

(65) Prior Publication Data
US 2024/0293090 A1 Sep. 5, 2024

Related U.S. Application Data

(63) Continuation of application No. 17/634,597, filed as application No. PCT/US2020/070500 on Sep. 4, 2020, now Pat. No. 11,992,348.
(Continued)

(51) Int. Cl.
*A61B 6/03* (2006.01)
*A61B 6/00* (2006.01)
(Continued)

(52) U.S. Cl.
CPC ............... *A61B 6/032* (2013.01); *A61B 6/12* (2013.01); *A61B 6/4085* (2013.01);
(Continued)

(58) Field of Classification Search
CPC ......... A61B 6/032; A61B 6/12; A61B 6/4085; A61B 6/4441; A61B 6/505; A61B 6/5258;
(Continued)

(56) References Cited

U.S. PATENT DOCUMENTS

| 11,992,348 B2 | 5/2024 | Unberath et al. |
| 2007/0003123 A1 | 1/2007 | Fu et al. |

(Continued)

FOREIGN PATENT DOCUMENTS

EP  3413773 B1  2/2020

OTHER PUBLICATIONS

Bier et al., "Learning to Detect Anatomical Landmarks of the Pelvis in X-rays From Arbitrary Views," International Journal of Computer Assisted Radiology and Surgery, 2019, vol. 14, pp. 1463-1473.
Castro W.H.M., et al., "Accuracy of Pedicle Screw Placement in Lumbar Vertebrae," Spine, 1996, vol. 11, pp. 1320-1324.
(Continued)

*Primary Examiner* — Mark R Gaworecki
(74) *Attorney, Agent, or Firm* — Harrity & Harrity, LLP

(57) ABSTRACT

A device may receive an X-ray image captured by a C-arm CBCT device at a particular position defined by a six-degree of freedom pose relative to an anatomy, and may process the X-ray image, with a machine learning model, to determine a predicted quality of next possible X-ray images provided by the C-arm CBCT device. The device may utilize the machine learning model, to identify a particular X-ray image, of the next possible X-ray images, with a greatest predicted quality and to update the six-degree of freedom pose based on the particular X-ray image. The device may provide, to the C-arm CBCT device, data that identifies the updated six-degree of freedom pose to cause the C-arm CBCT device to adjust to a new position based on the updated six-degree of freedom pose.

20 Claims, 10 Drawing Sheets

Related U.S. Application Data

(60) Provisional application No. 62/896,352, filed on Sep. 5, 2019.

(51) Int. Cl.

| | |
|---|---|
| *A61B 6/12* | (2006.01) |
| *A61B 6/40* | (2024.01) |
| *A61B 6/50* | (2024.01) |
| *G16H 20/40* | (2018.01) |
| *G16H 30/20* | (2018.01) |
| *G16H 30/40* | (2018.01) |

(52) U.S. Cl.
CPC ............ *A61B 6/4441* (2013.01); *A61B 6/505* (2013.01); *A61B 6/5258* (2013.01); *A61B 6/563* (2013.01); *G16H 20/40* (2018.01); *G16H 30/20* (2018.01); *G16H 30/40* (2018.01)

(58) Field of Classification Search
CPC ........ A61B 6/563; G16H 20/40; G16H 30/20; G16H 30/40
See application file for complete search history.

(56) References Cited

U.S. PATENT DOCUMENTS

| | | |
|---|---|---|
| 2009/0074151 A1 | 3/2009 | Henderson et al. |
| 2014/0334709 A1 | 11/2014 | Siewerdsen et al. |
| 2019/0000564 A1 | 1/2019 | Navab et al. |

OTHER PUBLICATIONS

Clark et al., "The Cancer Imaging Archive (TCIA): Maintaining and Operating a Public Information Repository," Journal of Digital Imaging, 2013, vol. 26, pp. 1045-1057.
Cordemans et al., "Accuracy of a New Intraoperative Cone Beam Ct Imaging Technique (Artis Zeego II) Compared to Postoperative Ct Scan for Assessment of Pedicle Screws Placement and Breaches Detection," European Spine Journal, 2017, vol. 26, pp. 2906-2916.
Dhillon K.S., Spinal Fusion for Chronic Low Back Pain: A Magic Bullet' or Wishful Thinking?, Malaysian Orthopaedic Journal, 2016, vol. 10 (1), pp. 61-68.
Egol K.A., et al., "Biomechanics of Locked Plates and Screws." Journal of Orthopaedic Trauma, 2004. vol. 18, pp. 488-493.
Feldkamp L.A., Practical Cone-beam Algorithm, Journal of the Optical Society of America, 1984, vol. 1 (6), pp. 612-619.
Gang G.J., et al., "Task-based Detectability in CT Image Reconstruction by Filtered Backprojection and Penalized Likelihood Estimation," Medical Physics, 2014, vol. 41, pp. 1-8.
Gao et al., "Localizing Dexterous Surgical Tools in X-ray for Image-based Navigation?," Cornell University, 2019, pp. 1-4.
Gelalis et al., "Accuracy of Pedicle Screw Placement: A Systematic Review of Prospective in Vivo Studies Comparing Free Hand, fluoroscopy Guidance and Navigation Techniques," European Spine Journal, 2012, vol. 21, pp. 247-255.
Gjesteby et al., "Metal Artifact Reduction in CT: Where Are We After Four Decades?," IEEE Access. 2016, vol. 4, pp. 5826-5849.
Huang et al., "An Evaluation of Three Commercially Available Metal .Artifact Reduction Methods for CT Imaging," Physics in Medicine and Biology, 2015, vol. 60, pp. 1047-1067.
International Search Report and Written Opinion for Application No. PCT/US2020/070500, mailed on Dec. 3, 2020, 6 pages.
Katsura et al., "Current and Novel Techniques for Metal Artifact Reduction at CT:Practical Guide for Radiologists," Radiographics : A Review Publication of the Radiological Society of North America, Inc, 2018, vol. 38(2), pp. 450-461.
Kosmopoulos et al., "Pedicle Screw Placement Accuracy," Spine, 2007, vol. 32, pp. E111-E120.
Mirza et al., "Systematic Review of Randomized Trials Comparing Lumbar Fusion Surgery to Nonoperative Care for Treatment of Chronic Back Pain," Spine, 2007, vol. 32, pp. 816-823.
Mnih et al., "Human-level Control Through Deep Reinforcement Learning." Nature, 2015, vol. 518(7540), pp. 529-533.
Parker et al., "Optimal Short Scan Convolution Reconstruction for Fanbeam CT," Technical Notes, 1982, vol. 9(2), pp. 254-257.
Patel et al., "Contrast-Enhanced Angiographic Cone-beam Ct of Cerebrovascular Stents: Experimental Optimization and Clinical Application," American Journal of Neuroradiology, 2011, vol. 32(1), pp. 137-144.
Pjontek et al., "Metal Artifact Reduction for Flat Panel Detector Intravenous Ct Angiography in Patients With intracranial Metallic Implants After Endovascular and Surgical Treatment," Journal of Neurointerventional Surgery, 2016, vol. 8(8), pp. 824-829.
Schmidhuber et al., "Deep Learning in Neural Networks: An Overview," Neural Networks, 2015, vol. 61, pp. 85-117.
Unberath et al., "Enabling Machine Learning in X-ray-Based Procedures via Realistic Simulation of Image Formation," International Journal of Computer Assisted Radiology and Surgery, 2019, vol. 14(9), pp. 1517-1528.
Van Der Bom et al., "Reduction of Coil Mass Artifacts in High-resolution Flat Detector Conebeam Ct of Cerebral Stent-assisted Coiling," AJNR. American Journal of Neuroradiology. 2013, vol. 34(11), pp. 2163-2170.

MACHINE LEARNING MODEL TO ADJUST C-ARM CONE-BEAM COMPUTED TOMOGRAPHY DEVICE TRAJECTORIES

RELATED APPLICATIONS

This application is a continuation of U.S. patent application Ser. No. 17/634,597 (now U.S. Pat. No. 11,992,348), filed Feb. 11, 2022, which is a 371 national stage of PCT Application PCT/US2020/070500, filed on Sep. 4, 2020, which claims priority to U.S. Provisional Patent Application No. 62/896,352, filed on Sep. 5, 2019, and entitled "TASK-AWARE AND ANATOMY-SPECIFIC CONE-BEAM COMPUTED TOMOGRAPHY," the contents of which are incorporated herein by reference in their entireties.

GOVERNMENT LICENSE RIGHTS

This invention was made with government support under EB028505 awarded by the National Institutes of Health. The government has certain rights in the invention.

BACKGROUND

Spinal fusion surgery is an operative therapy for chronic back pain with high economic burden, that is projected to further increase due to our aging society and our increasingly inactive lifestyle. Despite substantial improvements in operative technique, spinal fusion surgery remains high-risk. In addition to usual complications, pedicle screws that breach the cortex can result in nerve damage. Surprisingly, the number of misplaced pedicle screws remains high, with cortical breach occurring in up to 31% and 72% of the cases for freehand and fluoroscopy-guided techniques, respectively. Even when surgical navigation is employed, up to 19% of the screws are not fully contained in the cortex.

SUMMARY

In some implementations, a method may include receiving an X-ray image captured by a C-arm cone-beam computed tomography (CBCT) device at a particular position defined by a six-degree of freedom pose relative to an anatomy, and processing the X-ray image, with a machine learning model, to determine a predicted quality of next possible X-ray images provided by the C-arm CBCT device. The method may include utilizing the machine learning model to identify a particular X-ray image, of the next possible X-ray images, with a greatest predicted quality, and update the six-degree of freedom pose based on the particular X-ray image and to generate an updated six-degree of freedom pose. The method may include providing, to the C-arm CBCT device, data that identifies the six-degree of freedom pose, where the data that identifies the updated six-degree of freedom pose may cause the C-arm CBCT device to adjust to a new position based on the updated six-degree of freedom pose.

In some implementations, a device includes one or more memories, and one or more processors to receive an X-ray image captured by a C-arm CBCT device at a particular position defined by a six-degree of freedom pose relative to an anatomy, and process the X-ray image, with a machine learning model, to determine a predicted quality of next possible X-ray images provided by the C-arm CBCT device. The one or more processors may utilize the machine learning model to identify a particular X-ray image, of the next possible X-ray images, with a greatest predicted quality, and may utilize the machine learning model to update the six-degree of freedom pose based on the particular X-ray image and to generate an updated six-degree of freedom pose. The one or more processors may provide, to the C-arm CBCT device, data that identifies the updated six-degree of freedom pose, where the data that identifies the updated six-degree of freedom pose may cause the C-arm CBCT device to adjust to a new position based on the updated six-degree of freedom pose, and acquire a new X-ray image at the new position.

In some implementations, a non-transitory computer-readable medium may store a set of instructions that includes one or more instructions that, when executed by one or more processors of a device, cause the device to train a machine learning model based on a first dataset and a second dataset and to generate a trained machine learning model, and receive an X-ray image captured by a C-arm CBCT device at a particular position defined by a six-degree of freedom pose relative to an anatomy. The one or more instructions may cause the device to process the X-ray image, with the trained machine learning model, to determine a predicted quality of next possible X-ray images provided by the C-arm CBCT device, and utilize the trained machine learning model to identify a particular X-ray image, of the next possible X-ray images, with a greatest predicted quality. The one or more instructions may cause the device to utilize the trained machine learning model to update the six-degree of freedom pose based on the particular X-ray image and to generate an updated six-degree of freedom pose. The one or more instructions may cause the device to provide, to the C-arm CBCT device, data that identifies the updated six-degree of freedom pose, where the data that identifies the updated six-degree of freedom pose may cause the C-arm CBCT device to adjust to a new position based on the six-degree of freedom pose.

DETAILED DESCRIPTION OF PREFERRED EMBODIMENTS

Figure 1A:
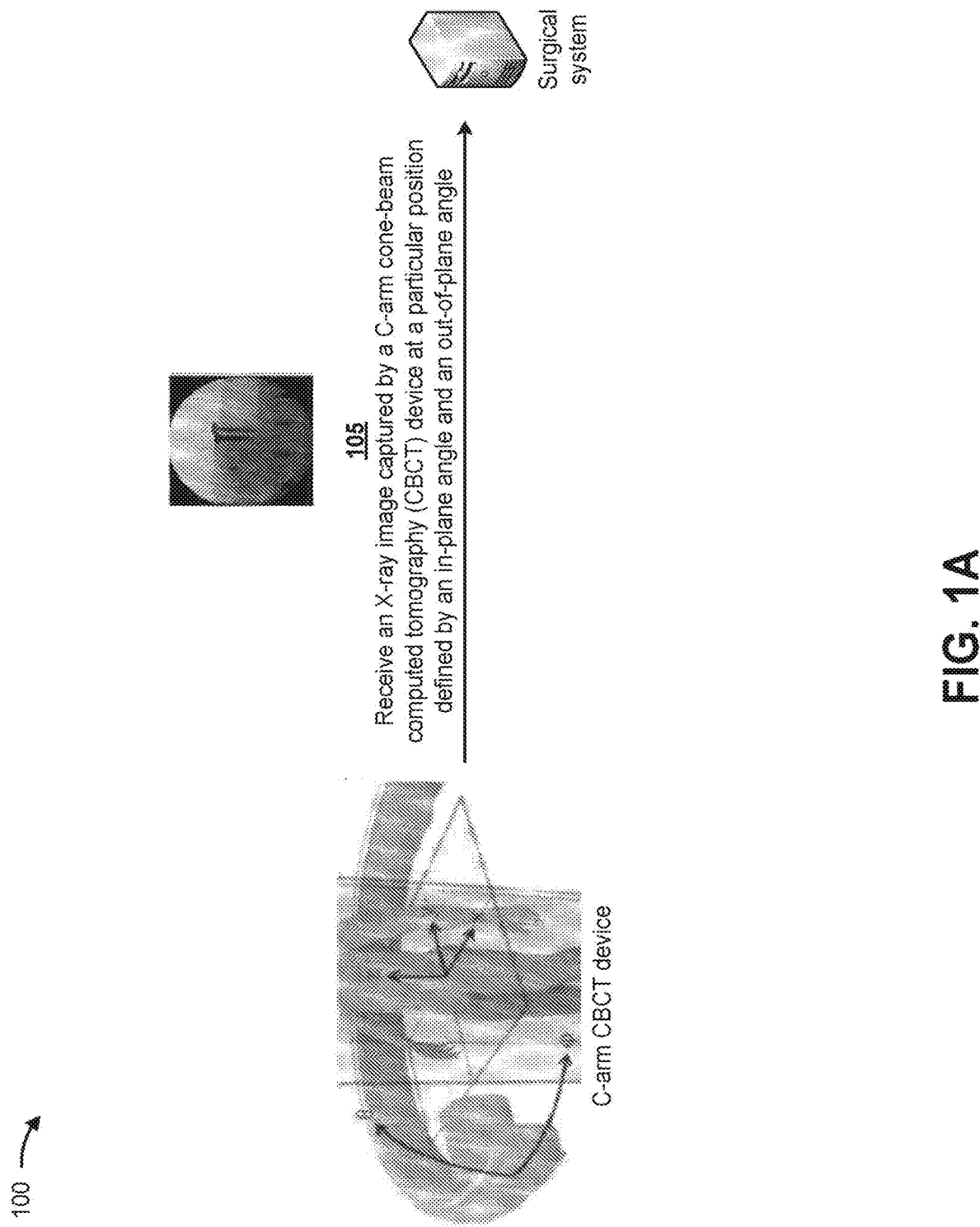
FIGS. 1A-1F are diagrams of one or more example implementations described herein.

The following detailed description of example implementations refers to the accompanying drawings. The same reference numbers in different drawings may identify the same or similar elements.

Currently, screw placement is assessed on post-operative computed tomography (CT) images, such that immediate repositioning of implants is not possible. Although intra-operative three-dimensional (3D) cone-beam CT (CBCT) device imaging with mobile and robotic C-arm X-ray systems is becoming widely available, it is not currently being used for spinal fusion 3D imaging, because compared to CT, C-arm CBCT device images suffer from substantially stronger metal artifacts around highly-attenuating titanium implants, which compromise a value of intra-operative CBCT for assessing cortical breach. An implication is that image quality must be improved, before CBCT is ready for high-volume applications, such as spinal fusion. Most current methods that seek to lift CBCT reconstruction quality to a clinical acceptance threshold limit themselves to include artifact propagation (e.g., via masking) or image-enhancement (e.g., streak reduction). These methods attempt to deal with artifacts after acquisition of the CBCT short-scan is already completed, and are thus limited by the already corrupted information present in the acquired X-ray projection images.

Thus, current techniques for utilizing C-arm CBCT images are inadequate and would waste computing resources (e.g., processing resources, memory resources, communication resources, and/or the like), networking resources, human resources, and/or the like associated with collecting inferior images via the C-arm CBCT device, incorrectly assessing cortical breach, attempting to correct the inferior images, and/or the like.

Some implementations described herein provide a surgical system that utilizes a machine learning model to adjust CBCT device trajectories for artifact avoidance. For example, the surgical system may receive an X-ray image captured by a C-arm CBCT device at a particular position defined by a six-degree of freedom pose relative to an anatomy, and may process the X-ray image, with a machine learning model, to determine a predicted quality of next possible X-ray images provided by the C-arm CBCT device. The surgical system may utilize the machine learning model to identify a particular X-ray image, of the next possible X-ray images, with a greatest predicted quality, and update the six-degree of freedom pose based on the particular X-ray image and to generate an updated six-degree of freedom pose. The surgical system may provide, to the C-arm CBCT device, data that identifies the updated six-degree of freedom pose, where the data that identifies the updated six-degree of freedom pose may cause the C-arm CBCT device to adjust to a new position based on the updated six-degree of freedom pose.

In this way, the surgical system utilizes a machine learning model to adjust CBCT device trajectories for artifact avoidance. The surgical system may extend the CBCT device trajectory by autonomously adjusting out-of-plane angulation, which enables CBCT device trajectories that are task-aware and scene-specific in that the trajectories avoid acquiring images with substantial corruption (e.g., beam hardening, photon starvation, noise, and/or the like). The recommendation and adjustment of ideal out-of-plane angulation may be performed on-the-fly using a machine learning model on a current two-dimensional (2D) X-ray projection image. Thus, the surgical system conserves computing resources, networking resources, human resources, and/or the like that would otherwise have been wasted in collecting inferior images via the C-arm CBCT device, incorrectly assessing cortical breach, attempting to correct the inferior images, and/or the like.

FIGS. 1A-1F are diagrams of one or more example implementations 100 associated utilizing a machine learning model to adjust CBCT device trajectories for artifact avoidance. As shown in FIG. 1A, example implementations 100 include a CBCT device and a surgical system. The CBCT device may include a device that performs a medical imaging technique that utilizes X-ray computed tomography, where X-rays are divergent and form a cone. The surgical system may include a system that utilizes a machine learning model to adjust CBCT device trajectories for artifact avoidance.

As further shown in FIG. 1A, and by reference number 105, the surgical system may receive an X-ray image captured by the C-arm CBCT device at a particular position (e.g., a trajectory) defined by a six-degree of freedom pose relative to an anatomy (e.g., an in-plane angle ($\varphi$) and an out-of-plane angle ($\theta$)). The X-ray image may include an X-ray image of a target object, such as a patient undergoing spinal fusion surgery, a particular location of the patient, and/or the like. The in-plane angle may be defined according to a traditional circular trajectory where a source and a detector of the C-arm CBCT device move in one plane for an entire scan. The out-of-plane angle may be associated with tilting the C-arm CBCT device relatively to the plane. Each trajectory may include a set of pairs ($\varphi_t$, $\theta_t$), t=0, ..., T, where T may correspond to a total quantity of projection images received from the C-arm CBCT device. The C-arm CBCT device may capture the X-ray image at the particular position ($\varphi_t$, $\theta_t$), and may provide the X-ray image to the surgical system.

Figure 1B:
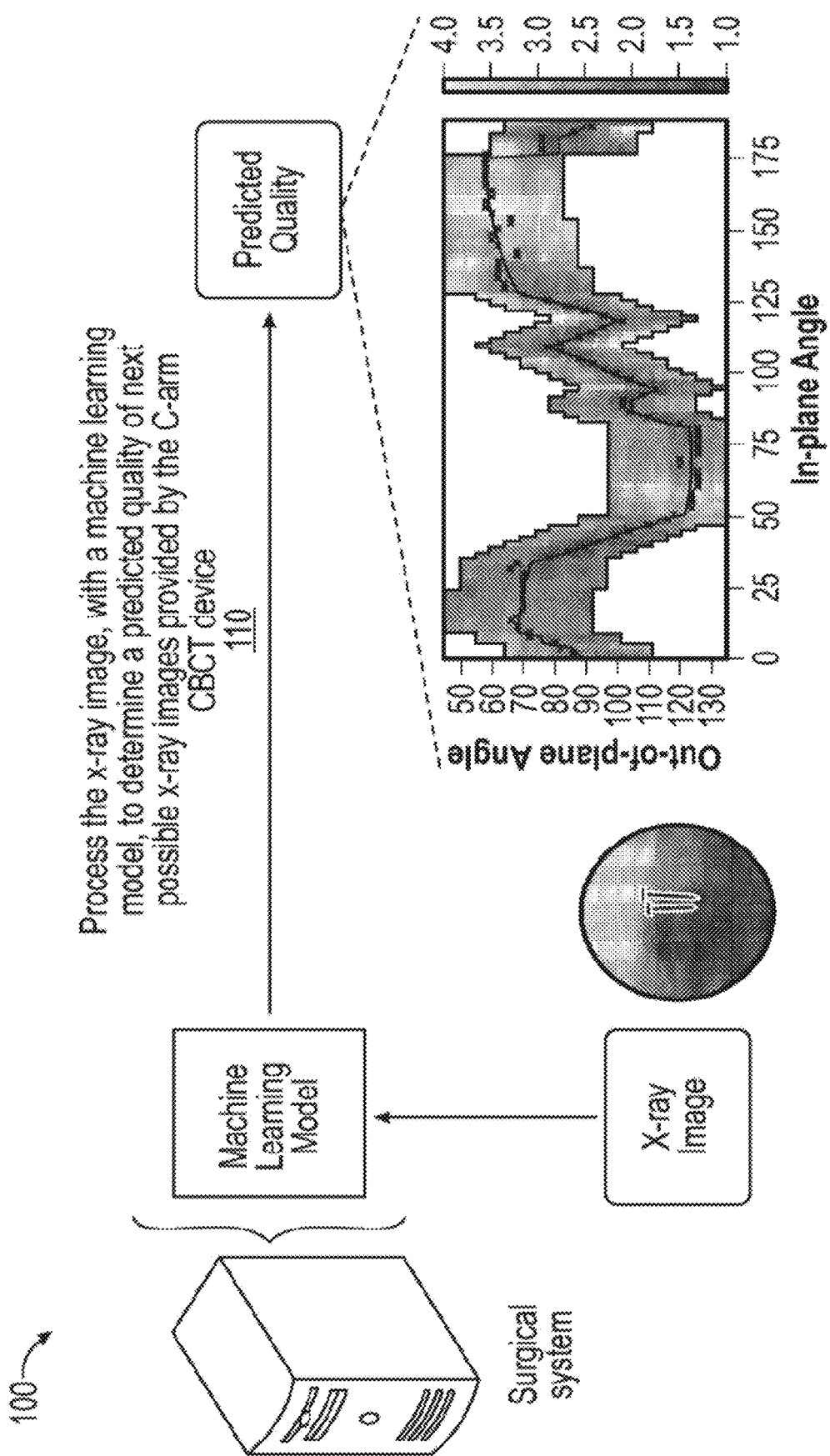

As shown in FIG. 1B, and by reference number 110, the surgical system may process the X-ray image, with a machine learning model, to determine a predicted quality of next possible X-ray images provided by the C-arm CBCT device. In some implementations, the machine learning model includes a visual geometry group (VGG)-type convolutional neural network model that regresses a detectability index for the next possible X-ray images provided by the C-arm CBCT device. Task-based trajectory optimization may rely on finding X-ray images that result in optimum reconstruction quality for a specific task. Therefore, the optimization may be contingent on assigning a task-optimality rank to X-ray images in a projection domain, and selecting views that are optimal in this metric. To assess how single X-ray images contribute to perceived reconstruction quality, the surgical system may utilize a matched filter observer model to calculate a detectability index ($d^2$) as follows:

$$d^2(\varphi, \theta) = \frac{\left[\int\int\int |MTF(\varphi, \theta)|^2 |W_{task}|^2 df_x df_y df_z\right]^2}{\int\int\int NPS(\varphi, \theta) |MTF(\varphi, \theta)|^2 |W_{task}|^2 df_x df_y df_z} \quad (1)$$

where $W_{task}$ may correspond to a task function describing properties of an object to be imaged with a highest quality in Fourier transform space, MTF may correspond to a local modulation transfer function, and NPS may correspond to a local noise power spectrum that depends on an X-ray image and, therefore, a relative pose of the C-arm CBCT device with respect to anatomy. For the case of iterative penalized-likelihood reconstruction, the surgical system may derive analytic equations for the MTF and the NPS. Such equations may rely on forward projecting voxels into all views contained in an X-ray image. The surgical system may compare projected values and measured values, and may back-project the compared values into the X-ray image. Using these calculations for the MTF and the NPS, the detectability index $d^2$ may depend on a three-dimensional structure of an imaged object in a set of images in a trajectory. When accurate three-dimensional information is available, equation (1) can be maximized with respect to $\varphi$ and $\theta$ to find an optimal trajectory. The MTF and the NPS are general measures that may be calculated by the surgical system for any imaged object. Although the detectability index is described herein as being utilized for metal artifacts, in some implementations, the detectability index may be utilized for other purposes, such as improving soft-tissue contrast.

Figure 1C:
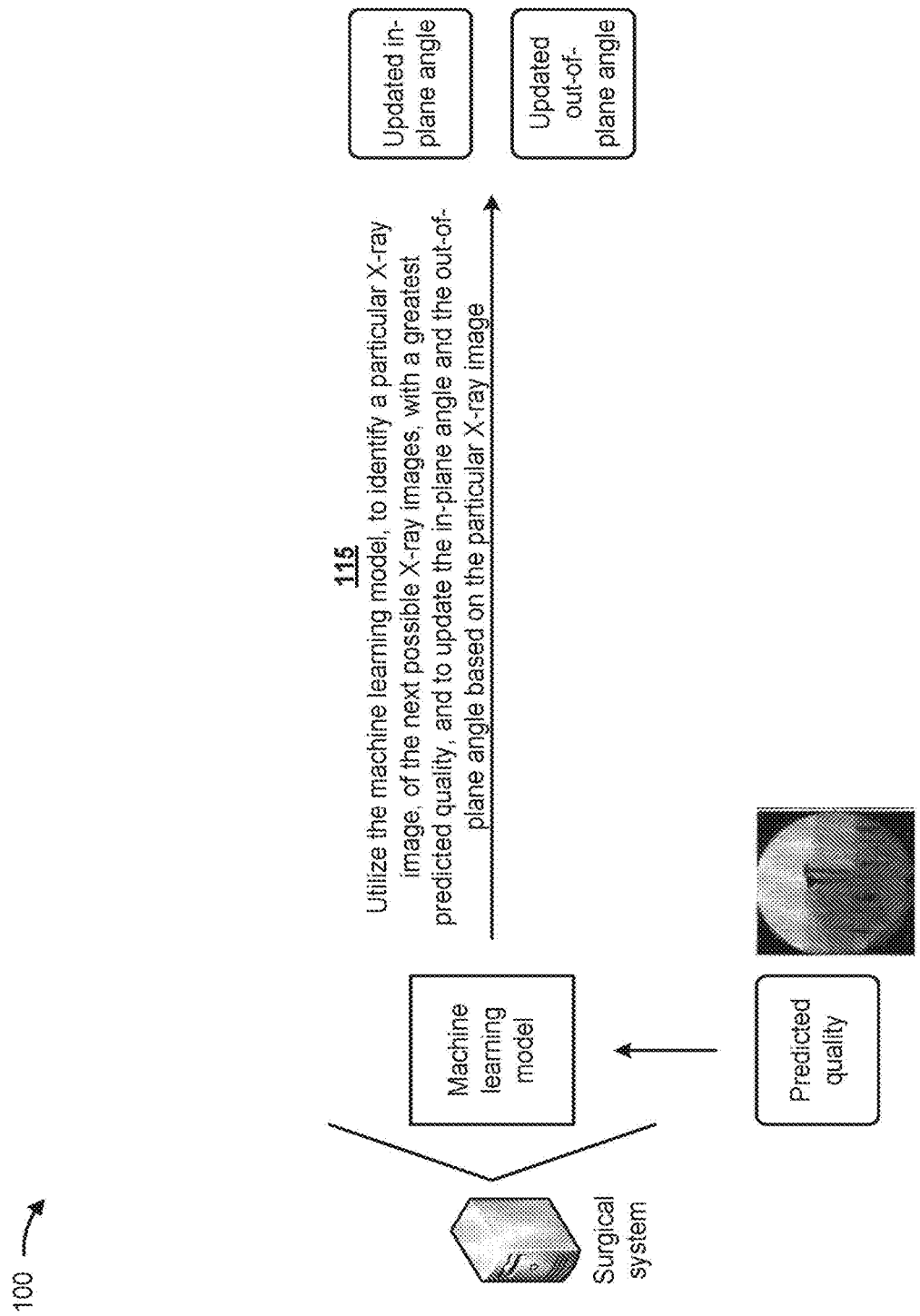

As shown in FIG. 1C, and by reference number 115, the surgical system may utilize the machine learning model to identify a particular X-ray image, of the next possible X-ray images, with a greatest predicted quality (e.g., detectability index), and to update the six-degree of freedom pose (e.g., the in-plane angle and the out-of-plane angle) based on the particular X-ray image. Thus, the surgical system may generate a new position for which the C-arm CBCT device is to adjust, where the new position is defined by the updated six-degree of freedom pose (e.g., the updated in-plane angle and the updated out-of-plane angle).

If the 3D patient anatomy is perfectly known, a complete trajectory can be optimized directly. However, this is not the case in surgical environments, where optimal view prediction may only depend on current and previous two-dimensional X-ray projections. The surgical system may utilize the detectability index calculated for each new possible next X-ray image as a quality function and may utilize the machine learning model to directly regress each next possible X-ray image from a current X-ray image. Acquiring an optimized trajectory may be achieved by selecting an out-of-plane angle ($\theta$) with a greatest predicted quality (e.g., detectability index), determining an adjustment or an update to the out-of-plane angle ($\theta$) as the C-arm CBCT device moves to a next in-plane angle ($\varphi$), and acquiring a next X-ray image at the updated position, that is then fed back into the machine learning model. The next possible X-ray images may be predicted, by the machine learning model, as X-ray images with an increment of five degrees (e.g., +5°) for the in-plane angle and a range of ±25° for the out-of-plane angle relative to a current position. The out-of-plane angle may be uniformly discretized in steps of 5° which may lead to eleven (11) values to be predicted for the X-ray image. This definition allows generating a training dataset, where all meaningful X-ray images, together with detectability indices, may be sampled on a uniform grid with step size of 5° in both $\varphi$ and $\theta$.

The machine learning model may be based on a VGG convolutional neural network model with modifications to perform regression instead of classification. Initial weights may be pre-trained and the machine learning model may be subsequently retrained on a task. During application, angle increments between two views may be below one degree, and linear interpolation may be used to predict a next best angle.

The machine learning model may be trained based on realistic digitally reconstructed radiographs (DRRs). For DRR generation, five chest CT volumes may be obtained from an archive. In every CT volume, six pairs of pedicle screws may be annotated and simulated leading to a total of thirty (30) different anatomical configurations, since only a single vertebral level may be considered at once. Data augmentation may be performed in three dimensions by randomly varying the C-arm CBCT device isocenter, yielding a dataset of two-hundred and twelve (212) scans with 290,016 X-ray images in total. A scan may include 1,368 X-ray images uniformly sampled on a truncated sphere with $\varphi \in (0°, 360°)$ and $\theta \in (45°, 135°)$, and with the detectability calculated as per Equation 1 for each X-ray image. To guarantee patient independence of training and test, splitting of data may be performed on a CT level, where four volumes (e.g., 176 scans) may be used for training and one volume (e.g., 36 scans) may be used for test and validation.

The X-ray images may be saved both noise-free and with noise corresponding to a fluence of 20,000 photons emitted towards every pixel. The noise free images may be used to calculate ground-truth detectability, while the noisy images may be used as input during training of the machine learning model. This approach ensures that detectability maps are an optimum learning target, while the machine learning model becomes invariant to noisy observations as they would occur in real X-ray images.

For experiments on real data, a set of analytic phantoms (e.g., squares, cylinders, screw model, and/or the like) that represent a chest may be implemented and a second in silico dataset may be generated. The dataset may include 75 scans, generated with a same setup as described above for the synthetic data experiments, except for a photonfluence of 500 photons per pixel, adapted to a smaller size of the phantom.

A trajectory optimization may be tested on six different vertebral levels in a separate test volume. As direct evaluation of the training loss function may not represent a quality of the selected trajectory, two surrogate measures may be defined. An angular distance of a predicted next-best action to a best action selected from ground truth data may measure a spatial difference between predicted and optimal trajectory. While the angular error may be an intuitive and interpretable measure, it may not fully capture a performance of the process. Even if an angular distance of a selected action is high, it can still result in a close to optimal reconstruction performance, as a function of detectability values can be multimodal. Therefore, a difference in detectability between a predicted next action and an optimal next action may be introduced as a better measure for reconstruction performance. On a test set, these performance metrics may be evaluated to 8.35°±11.61° for an angular distance error and 13.69%±18.92% degradation in detectability.

In some implementations, the surgical system trains the machine learning model based on a first dataset and a second dataset, and prior to receiving the X-ray image. The first dataset may be based on historical human chest CT images, and the second dataset may be based on a semi-anthropomorphic representation of a human chest. In some implementations, the surgical system utilizes a synthetic dataset to test the machine learning model prior to receiving the X-ray image, utilizes a real dataset to train the machine learning model prior to receiving the X-ray image, and utilizes batch normalization and data augmentation with the machine learning model prior to receiving the X-ray image.

Figure 1D:
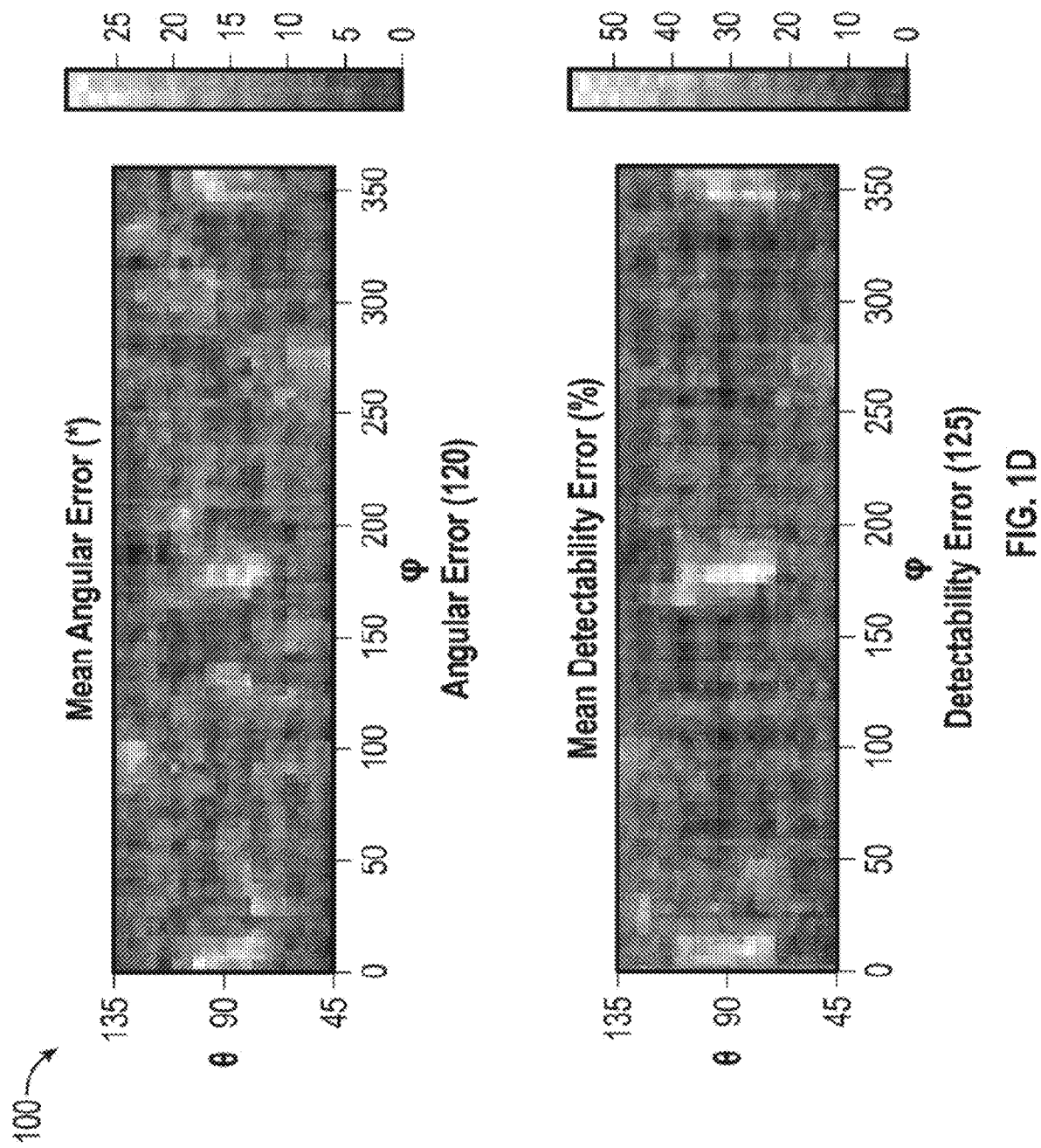

A spatial distribution of an average degradation of detectability in the test set is illustrated in FIG. 1D. As shown in FIG. 1D, and by reference number 120, a mean angular error (in degrees) may be calculated for different in-plane angles ($\varphi$) and different out-of-plane angles ($\theta$). As further shown in FIG. 1D, and by reference number 125, a mean detectability error (in percentage) may be calculated for different in-plane angles ($\varphi$) and different out-of-plane angles ($\theta$).

Besides a quality of selected actions, stability with respect to noise may be needed for applications. A comparison of an average distance between trajectories predicted from noise-free data to noisy samples generated with 400,000, 100,000, and 50,000 photons per pixel may be performed to generate measures of 0.83°±1.56°, 1.13°±1.63°, and 1.64°±1.73°, respectively, for different noise levels.

When the C-arm CBCT device is used for intra-operative imaging, optimal alignment between the C-arm CBCT device and a patient's anatomy may not be ensured. Therefore, robustness for different initialization angles may be required (e.g., the machine learning model may transition into a same or equivalent trajectory irrespective of initialization). This may be achieved via a Markov property, where detectability indices used for optimizing the trajectory may depend on a last acquired X-ray image and not on a history of the trajectory. Therefore, as soon as two trajectories would intersect each other, they may merge into a single trajectory.

Figure 1E:
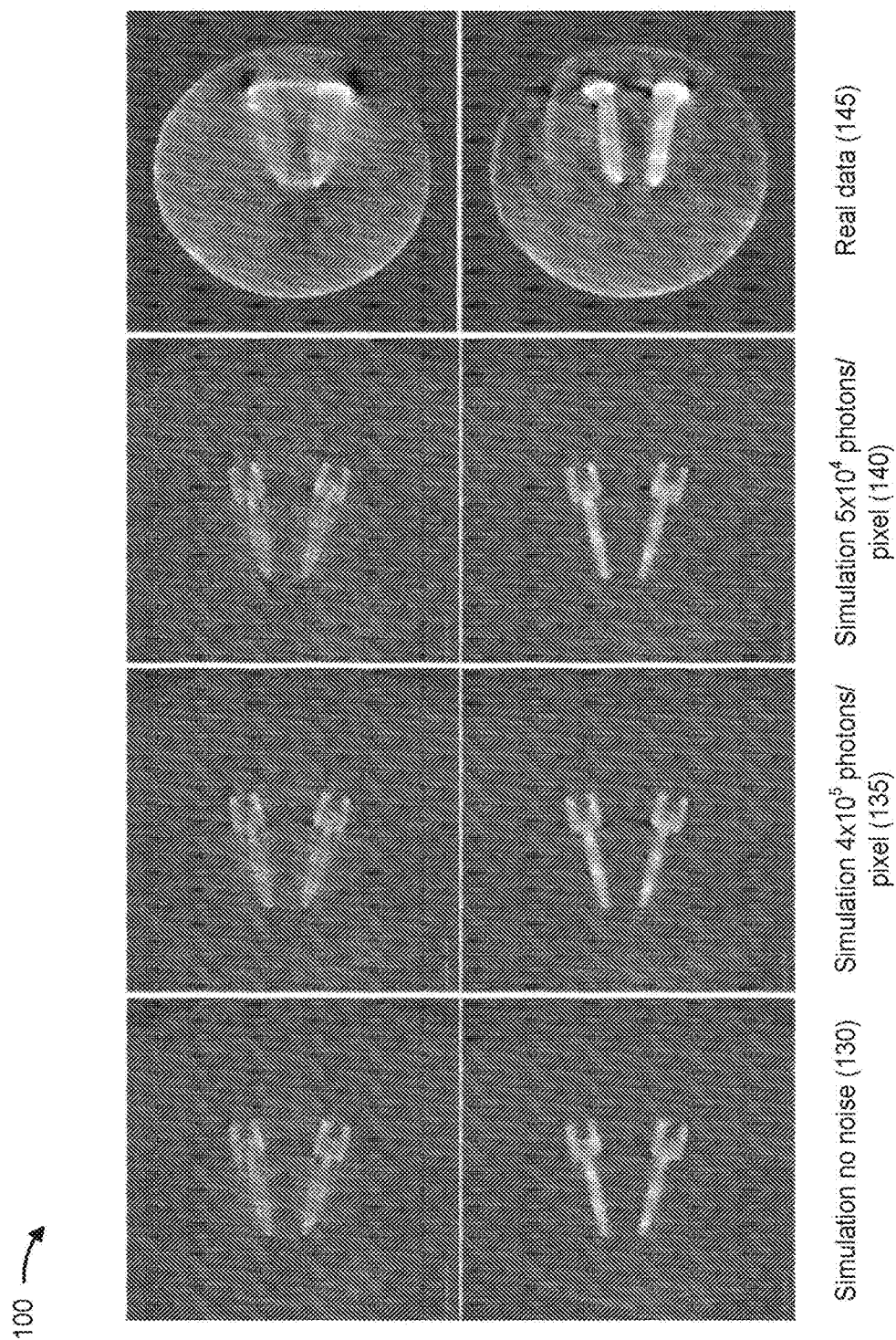

For the synthetic test data, examples of representative reconstructions from a short-scan and a task-aware trajectory are shown in FIG. 1E. Both volumes may be reconstructed using iterative conjugated gradients least-squares (e.g., an ASTRA Toolbox) from noise-free projections. For the proposed task-aware trajectory, the screw is more homogeneous and exhibits less cupping artifact, and metal artifacts (bright and dark streaks) are reduced, enabling better assessment of bony anatomy in close proximity to the implant.

As shown in FIG. 1E, and by reference number 130, a simulation of artifacts with no noise may be reconstructed. As shown by reference number 135, a simulation of the artifacts with $4 \times 10^5$ photons/pixel may be reconstructed. As shown by reference number 140, a simulation of the artifacts with $5 \times 10^4$ photons/pixel may also be reconstructed.

As further shown in FIG. 1E, and by reference number 145, artifacts from real data may be reconstructed. The real data experiments may be performed on a physical phantom that includes two ballistic gel cylinders mounted on a wooden beam with two iron screws, abstractly mimicking the human chest. The C-arm CBCT device may acquire five CBCT short-scans, performed with inclinations ranging from large negative values (e.g., approximately −30°) to large positive values (e.g., approximately 30°). Corresponding reconstructions obtained with filtered back-projection may also be obtained from the C-arm CBCT device.

The detectability of next possible views may be predicted with the machine learning model trained on the analytic phantom dataset. As an available C-arm CBCT device geometry may currently limit reconstruction to circular trajectories, a quality of a best circular scan may be compared with a conventional circular scan. The best circular scan may be determined by accumulating a predicted detectability for $\Delta\theta=0$, which closely models an overall task. Via this approach, a scan with a highest positive tilt may be selected, yielding a 19.0% increase in predicted detectability compared to a conventional scan.

A highest predicted detectability at any given time may be highlighted, which corresponds to the unregularized manipulation commands that would be sent to the C-arm CBCT device. Curves close to a centerline may indicate small C-arm CBCT device adjustments, while curves far from the centerline may imply an attempt to drive the C-arm CBCT device out of a central plane. Large out-of-plane angle commands may be observed for scans with low absolute tilt (e.g., conventional), and minimal deviation for scans with high tilt, indicating a close to optimal trajectory. Such behavior may be interpretable and the surgical system may attempt to prevent images with screw overlap, thus reducing metal artifacts in a reconstruction. The reconstruction from the high-tilt trajectory recommended by the surgical system may exhibit a notable reduction of metal artifacts and noise, and may reveal a screw thread that is completely invisible in conventional systems. Thus, the surgical system provides overall image quality improvements when using C-arm CBCT devices with at-panel detectors and more brilliant X-ray sources.

Figure 1F:
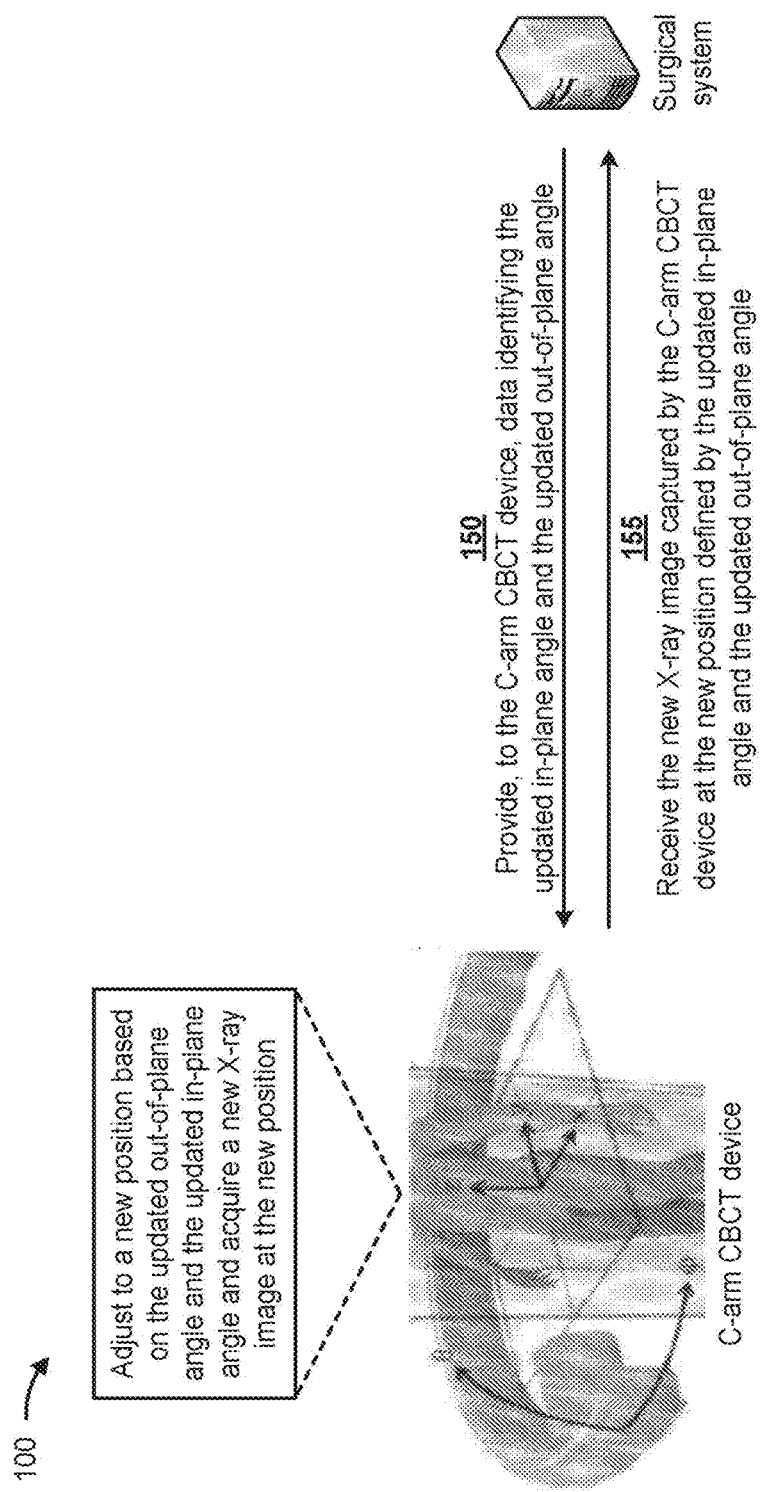

As shown in FIG. 1F, and by reference number 150, the surgical system may provide, to the C-arm CBCT device, data identifying the updated six-degree of freedom pose (e.g., the updated in-plane angle and the updated out-of-plane angle). For example, the surgical system may provide, to the C-arm CBCT device, data identifying a new position for which the C-arm CBCT device is to adjust, where the new position is defined by the updated in-plane angle and the updated out-of-plane angle. The C-arm CBCT device may adjust to the new position based on the updated out-of-plane angle and the updated in-plane angle, and may acquire a new X-ray image (e.g., of a target object, such as a patient's spine) at the new position.

As further shown in FIG. 1F, and by reference number 155, the surgical system may receive the new X-ray image captured by the C-arm CBCT device at the new position defined by the updated six-degree of freedom pose (e.g., the updated in-plane angle and the updated out-of-plane angle). In some implementations, the surgical system processes the new X-ray image as described in connection with FIGS. 1B and 1C, and generates another new position for which the C-arm CBCT device is to adjust, where the other new position is defined by another updated in-plane angle and another updated out-of-plane angle. In some implementations, the surgical system identifies a problem with a spinal fusion surgery based on one or more of the X-ray image or the next possible X-ray images, and provides a notification that identifies the problem.

In this way, the surgical system utilizes a machine learning model to adjust CBCT device trajectories for artifact avoidance. The surgical system may extend the CBCT device trajectory by autonomously adjusting out-of-plane angulation, which enables CBCT device trajectories that are task-aware and scene-specific in that the trajectories avoid acquiring images with substantial corruption (e.g., beam hardening, photon starvation, noise, and/or the like). Furthermore, the surgical system enables scene-specific source trajectories in clinical settings, where only little prior information is available, recommends viewing angles onto anatomy, and is combinable with any reconstruction or metal artifact reduction technique. Thus, the surgical system conserves computing resources, networking resources, human resources, and/or the like that would otherwise have been wasted in collecting inferior images via the C-arm CBCT device, incorrectly assessing cortical breach, attempting to correct the inferior images, and/or the like.

As indicated above, FIGS. 1A-1F are provided as an example. Other examples may differ from what is described with regard to FIGS. 1A-1F. The number and arrangement of devices shown in FIGS. 1A-1F are provided as an example. In practice, there may be additional devices, fewer devices, different devices, or differently arranged devices than those shown in FIGS. 1A-1F. Furthermore, two or more devices shown in FIGS. 1A-1F may be implemented within a single device, or a single device shown in FIGS. 1A-1F may be implemented as multiple, distributed devices. Additionally, or alternatively, a set of devices (e.g., one or more devices) shown in FIGS. 1A-1F may perform one or more functions described as being performed by another set of devices shown in FIGS. 1A-1F.

Figure 2:
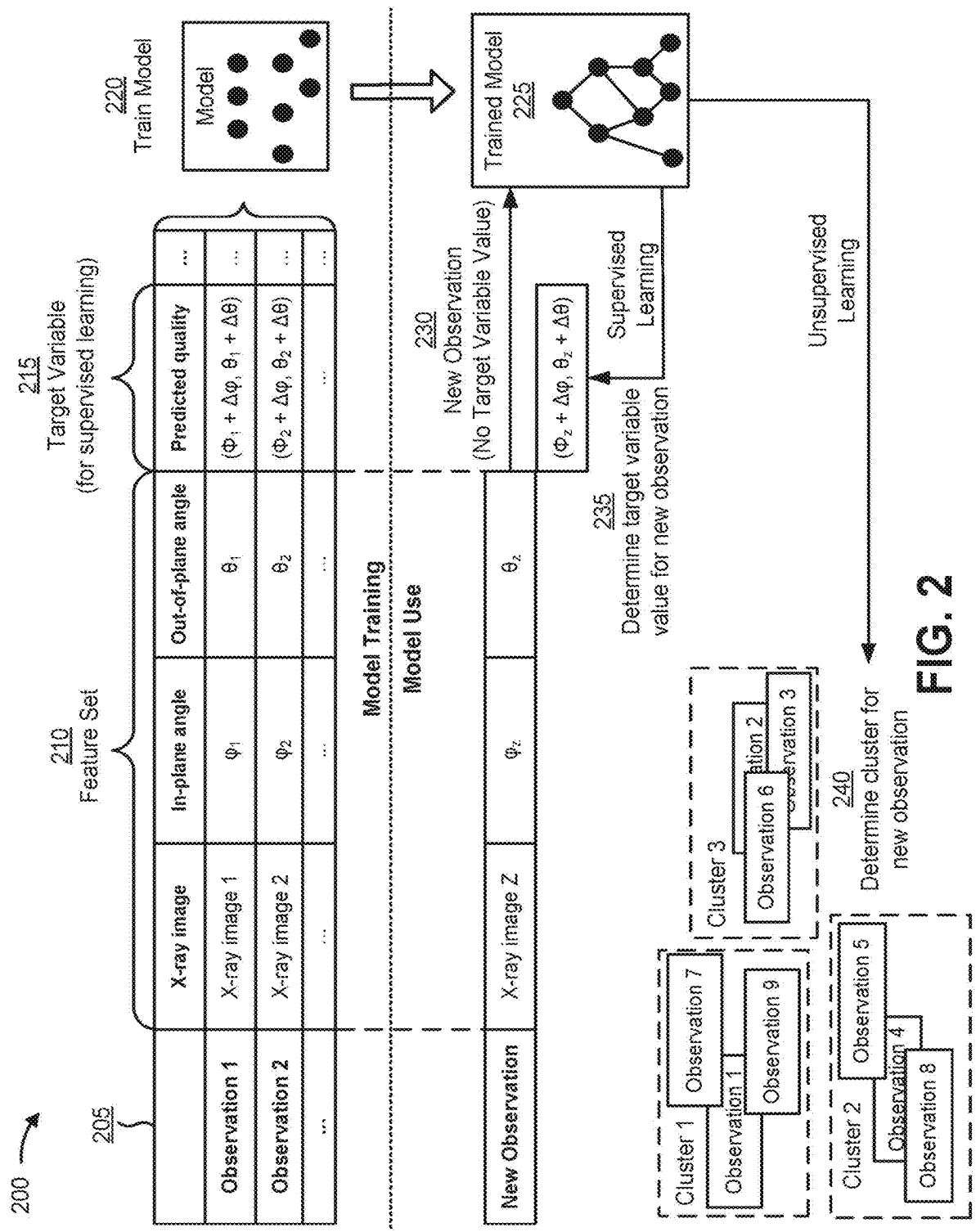
FIG. 2 is a diagram illustrating an example of training a machine learning model and applying a trained machine learning model to a new observation.

FIG. 2 is a diagram illustrating an example 200 of training and using a machine learning model in connection with adjusting CBCT device trajectories for artifact avoidance. The machine learning model training and usage described herein may be performed using a machine learning system. The machine learning system may include or may be included in a computing device, a server, a cloud computing environment, and/or the like, such as the surgical system described in more detail elsewhere herein.

As shown by reference number 205, a machine learning model may be trained using a set of observations. The set of observations may be obtained from historical data, such as data gathered during one or more processes described herein. In some implementations, the machine learning system may receive the set of observations (e.g., as input) from the CBCT device, as described elsewhere herein.

As shown by reference number 210, the set of observations includes a feature set. The feature set may include a set of variables, and a variable may be referred to as a feature. A specific observation may include a set of variable values (or feature values) corresponding to the set of variables. In some implementations, the machine learning system may determine variables for a set of observations and/or variable values for a specific observation based on input received from the CBCT device. For example, the machine learning system may identify a feature set (e.g., one or more features and/or feature values) by extracting the feature set from structured data, by performing natural language processing to extract the feature set from unstructured data, by receiving input from an operator, and/or the like.

As an example, a feature set for a set of observations may include a first feature of X-ray images, a second feature of in-plane angles, a third feature of out-of-plane angles, and so on. As shown, for a first observation, the first feature may include a first X-ray image (e.g., X-ray image 1), the second feature may include a first in-plane angle (e.g., $\varphi_1$), the third feature may include a first out-of-plane angle (e.g., $\theta_1$), and so on. These features and feature values are provided as examples, and may differ in other examples. For example, the feature set may include one or more of the following features: X-ray images captured by the CBCT device, in-plane angles associated with the X-ray images, out-of-plane angles associated with the X-ray images, and/or the like.

As shown by reference number 215, the set of observations may be associated with a target variable. The target variable may represent a variable having a numeric value, may represent a variable having a numeric value that falls within a range of values or has some discrete possible values, may represent a variable that is selectable from one of multiple options (e.g., one of multiple classes, classifications, labels, and/or the like), may represent a variable having a Boolean value, and/or the like. A target variable may be associated with a target variable value, and a target variable value may be specific to an observation. In example 200, the target variable is a predicted quality of next possible projections (e.g., X-ray images) received from the CBCT device.

The feature set and target variable described above are provided as examples, and other examples may differ from what is described above. For example, for a target variable of the predicted quality of next possible projections, the feature set may include values associated with the predicted quality, in-plane angles associated with the next possible projections, out-of-plane angles associated with the next possible projections, and/or the like.

The target variable may represent a representation that a machine learning model is being trained to predict, and the feature set may represent the variables that are input to a trained machine learning model to predict a value for the target variable. The set of observations may include target variable values so that the machine learning model can be trained to recognize patterns in the feature set that lead to a target variable value. A machine learning model that is trained to predict a target variable value may be referred to as a supervised learning model.

In some implementations, the machine learning model may be trained on a set of observations that do not include a target variable. This may be referred to as an unsupervised learning model. In this case, the machine learning model may learn patterns from the set of observations without labeling or supervision, and may provide output that indicates such patterns, such as by using clustering and/or association to identify related groups of items within the set of observations.

As shown by reference number 220, the machine learning system may train a machine learning model using the set of observations and using one or more machine learning algorithms, such as a regression algorithm, a decision tree algorithm, a neural network algorithm, a k-nearest neighbor algorithm, a support vector machine algorithm, and/or the like. After training, the machine learning system may store the machine learning model as a trained machine learning model 225 to be used to analyze new observations.

As shown by reference number 230, the machine learning system may apply the trained machine learning model 225 to a new observation, such as by receiving a new observation and inputting the new observation to the trained machine learning model 225. As shown, the new observation may include a first feature of a zth X-ray image (e.g., X-ray image Z), a second feature of a zth in-plane angle (e.g., $\varphi_z$), a third feature of a zth out-of-plane angle (e.g., $\theta_z$), and so on, as an example. The machine learning system may apply the trained machine learning model 225 to the new observation to generate an output (e.g., a result). The type of output may depend on the type of machine learning model and/or the type of machine learning task being performed. For example, the output may include a predicted value of a target variable, such as when supervised learning is employed. Additionally, or alternatively, the output may include information that identifies a cluster to which the new observation belongs, information that indicates a degree of similarity between the new observation and one or more other observations, and/or the like, such as when unsupervised learning is employed.

As an example, the trained machine learning model 225 may determine a predicted quality of next possible projections (e.g., X-ray images) received from the CBCT device based on the new observation, as shown by reference number 235. Based on this prediction, the machine learning system may provide a first recommendation, may provide output for determination of a first recommendation, may perform a first automated action, may cause a first automated action to be performed (e.g., by instructing another device to perform the automated action), and/or the like. The first recommendation may include, for example, an updated in-plane angle and an updated out-of-plane angle for a next possible projection with a greatest value. The first automated action may include, for example, providing the updated in-plane angle and the updated out-of-plane angle to the CBCT device.

In some implementations, the trained machine learning model 225 may classify (e.g., cluster) the new observation in a cluster, as shown by reference number 240. The observations within a cluster may have a threshold degree of similarity. As an example, if the machine learning system classifies the new observation in a first cluster (e.g., the updated in-plane angle and the updated out-of-plane angle), then the machine learning system may provide a first recommendation, such as the first recommendation described above. Additionally, or alternatively, the machine learning system may perform a first automated action and/or may cause a first automated action to be performed (e.g., by providing the updated in-plane angle and the updated out-of-plane angle to the CBCT device) based on classifying the new observation in the first cluster, such as the first automated action described above.

In some implementations, the recommendation and/or the automated action associated with the new observation may be based on a target variable value having a particular label (e.g., classification, categorization, and/or the like), may be based on whether a target variable value satisfies one or more thresholds (e.g., whether the target variable value is greater than a threshold, is less than a threshold, is equal to a threshold, falls within a range of threshold values, and/or the like), may be based on a cluster in which the new observation is classified, and/or the like.

In this way, the machine learning system may apply a rigorous and automated process to adjust CBCT device trajectories for artifact avoidance. The machine learning system enables recognition and/or identification of tens, hundreds, thousands, or millions of features and/or feature values for tens, hundreds, thousands, or millions of observations, thereby increasing accuracy and consistency and reducing delay associated with adjusting CBCT device trajectories for artifact avoidance relative to requiring computing resources to be allocated for tens, hundreds, or thousands of operators to manually adjust CBCT device trajectories for artifact avoidance using the features or feature values.

As indicated above, FIG. 2 is provided as an example. Other examples may differ from what is described in connection with FIG. 2.

Figure 3:
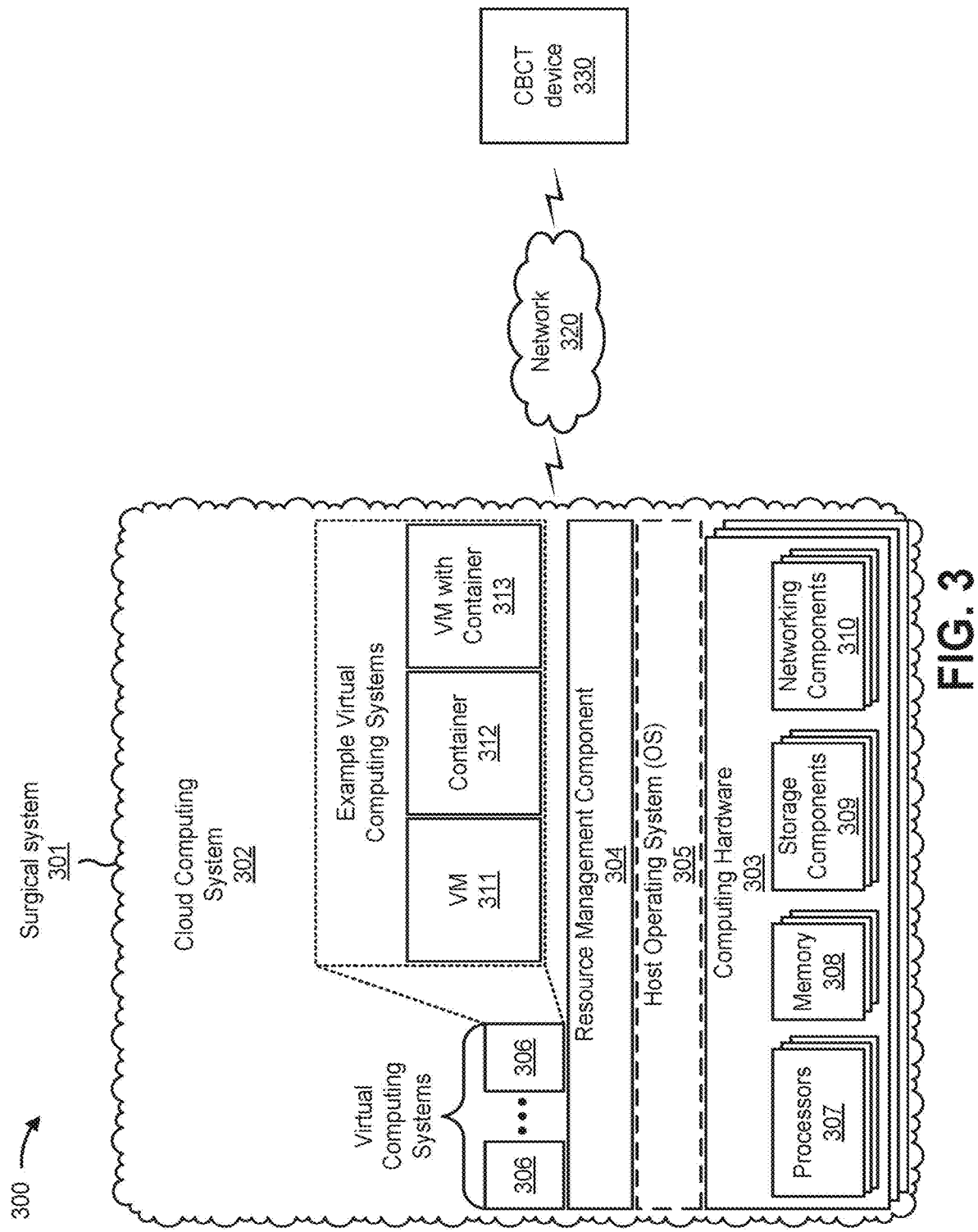
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a surgical system 301, which may include one or more elements of and/or may execute within a cloud computing system 302. The cloud computing system 302 may include one or more elements 303-313, as described in more detail below. As further shown in FIG. 3, environment 300 may include a network 320 and/or a CBCT device 330. Devices and/or elements of environment 300 may interconnect via wired connections and/or wireless connections.

The cloud computing system 302 includes computing hardware 303, a resource management component 304, a host operating system (OS) 305, and/or one or more virtual computing systems 306. The resource management component 304 may perform virtualization (e.g., abstraction) of computing hardware 303 to create the one or more virtual computing systems 306. Using virtualization, the resource management component 304 enables a single computing device (e.g., a computer, a server, and/or the like) to operate like multiple computing devices, such as by creating multiple isolated virtual computing systems 306 from computing hardware 303 of the single computing device. In this way, computing hardware 303 can operate more efficiently, with lower power consumption, higher reliability, higher availability, higher utilization, greater flexibility, and lower cost than using separate computing devices.

Computing hardware 303 includes hardware and corresponding resources from one or more computing devices. For example, computing hardware 303 may include hardware from a single computing device (e.g., a single server) or from multiple computing devices (e.g., multiple servers), such as multiple computing devices in one or more data centers. As shown, computing hardware 303 may include one or more processors 307, one or more memories 308, one or more storage components 309, and/or one or more networking components 310. Examples of a processor, a memory, a storage component, and a networking component (e.g., a communication component) are described elsewhere herein.

The resource management component 304 includes a virtualization application (e.g., executing on hardware, such as computing hardware 303) capable of virtualizing computing hardware 303 to start, stop, and/or manage one or more virtual computing systems 306. For example, the resource management component 304 may include a hypervisor (e.g., a bare-metal or Type 1 hypervisor, a hosted or Type 2 hypervisor, and/or the like) or a virtual machine monitor, such as when the virtual computing systems 306 are virtual machines 311. Additionally, or alternatively, the resource management component 304 may include a container manager, such as when the virtual computing systems 306 are containers 312. In some implementations, the resource management component 304 executes within and/or in coordination with a host operating system 305.

A virtual computing system 306 includes a virtual environment that enables cloud-based execution of operations and/or processes described herein using computing hardware 303. As shown, a virtual computing system 306 may include a virtual machine 311, a container 312, a hybrid environment 313 that includes a virtual machine and a container, and/or the like. A virtual computing system 306 may execute one or more applications using a file system that includes binary files, software libraries, and/or other resources required to execute applications on a guest operating system (e.g., within the virtual computing system 306) or the host operating system 305.

Although surgical system 301 may include one or more elements 303-313 of the cloud computing system 302, may execute within the cloud computing system 302, and/or may be hosted within the cloud computing system 302, in some implementations, surgical system 301 may not be cloud-based (e.g., may be implemented outside of a cloud computing system) or may be partially cloud-based. For example, surgical system 301 may include one or more devices that are not part of the cloud computing system 302, such as device 400 of FIG. 4, which may include a stand-alone server or another type of computing device. Surgical system 301 may perform one or more operations and/or processes described in more detail elsewhere herein.

Network 320 includes one or more wired and/or wireless networks. For example, network 320 may include a cellular network, a public land mobile network (PLMN), a local area network (LAN), a wide area network (WAN), a private network, the Internet, and/or the like, and/or a combination of these or other types of networks. The network 320 enables communication among the devices of environment 300.

CBCT device 330 includes one or more devices capable of receiving, generating, storing, processing, and/or providing information, such as information described herein. For example, CBCT device 330 may include a device that utilizes X-ray computed tomography, where X-rays are divergent and form a cone. During imaging, CBCT device 330 rotates around a body part of a patient, and may obtain hundreds of distinct X-ray images. For interventional radiology, a patient is positioned offset to CBCT device 330 so that a region of interest is centered in a field of view for the cone beam. A single two-hundred degree rotation by CBCT device 330, over the region of interest, acquires a volumetric data set. CBCT device 330 collects the data and reconstructs the data, producing a digital volume composed of three-dimensional voxels of anatomical data that can then be manipulated and visualized.

The number and arrangement of devices and networks shown in FIG. 3 are provided as an example. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
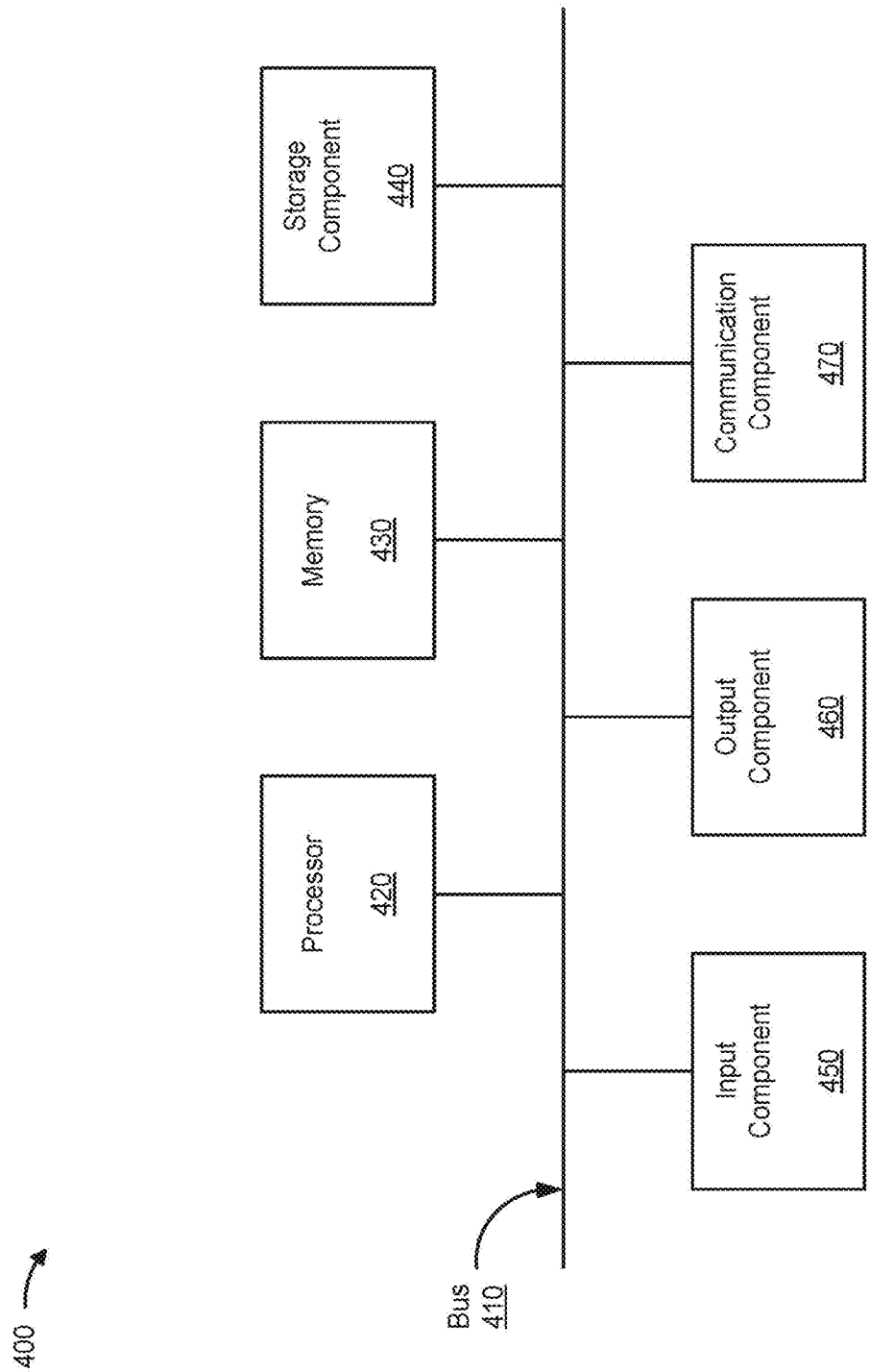
FIG. 4 is a diagram of example components of one or more devices of FIG. 3.

FIG. 4 is a diagram of example components of a device 400, which may correspond to surgical system 301, computing hardware 303, and/or CBCT device 330. In some implementations, surgical system 301, computing hardware 303, and/or CBCT device 330 may include one or more devices 400 and/or one or more components of device 400. As shown in FIG. 4, device 400 may include a bus 410, a processor 420, a memory 430, a storage component 440, an input component 450, an output component 460, and a communication component 470.

Bus 410 includes a component that enables wired and/or wireless communication among the components of device 400. Processor 420 includes a central processing unit, a graphics processing unit, a microprocessor, a controller, a microcontroller, a digital signal processor, a field-programmable gate array, an application-specific integrated circuit, and/or another type of processing component. Processor 420 is implemented in hardware, firmware, or a combination of hardware and software. In some implementations, processor 420 includes one or more processors capable of being programmed to perform a function. Memory 430 includes a random access memory), a read only memory, and/or another type of memory (e.g., a flash memory, a magnetic memory, and/or an optical memory).

Storage component 440 stores information and/or software related to the operation of device 400. For example, storage component 440 may include a hard disk drive, a magnetic disk drive, an optical disk drive, a solid state disk drive, a compact disc, a digital versatile disc, and/or another type of non-transitory computer-readable medium. Input component 450 enables device 400 to receive input, such as user input and/or sensed inputs. For example, input component 450 may include a touch screen, a keyboard, a keypad, a mouse, a button, a microphone, a switch, a sensor, a global positioning system component, an accelerometer, a gyroscope, an actuator, and/or the like. Output component 460 enables device 400 to provide output, such as via a display, a speaker, and/or one or more light-emitting diodes. Communication component 470 enables device 400 to communicate with other devices, such as via a wired connection and/or a wireless connection. For example, communication component 470 may include a receiver, a transmitter, a transceiver, a modem, a network interface card, an antenna, and/or the like.

Device 400 may perform one or more processes described herein. For example, a non-transitory computer-readable medium (e.g., memory 430 and/or storage component 440) may store a set of instructions (e.g., one or more instructions, code, software code, program code, and/or the like) for execution by processor 420. Processor 420 may execute the set of instructions to perform one or more processes described herein. In some implementations, execution of the set of instructions, by one or more processors 420, causes the one or more processors 420 and/or the device 400 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 4 are provided as an example. Device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
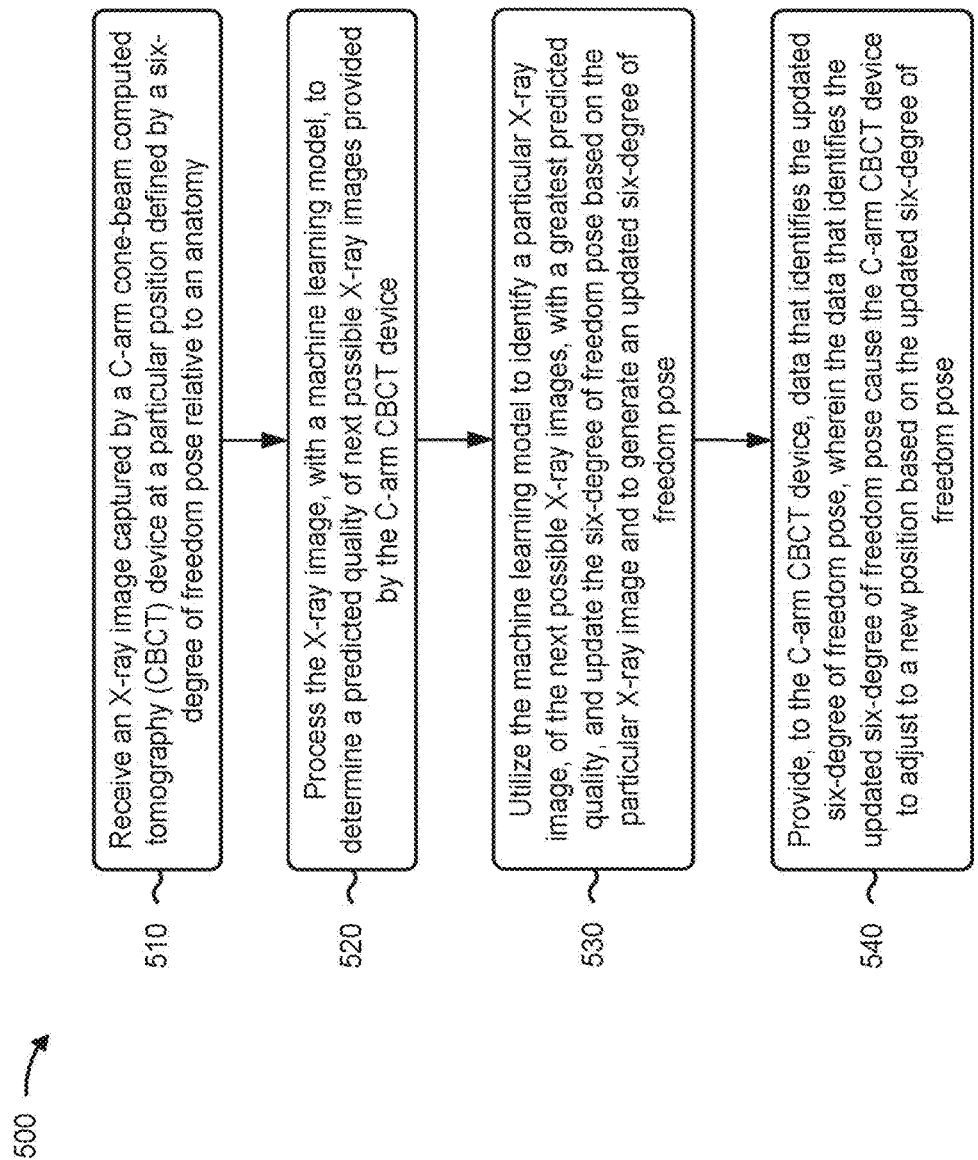
FIG. 5 is a flow chart of an example process for utilizing a machine learning model to adjust C-arm cone-beam computed tomography (CBCT) device trajectories for artifact avoidance.

FIG. 5 is a flowchart of an example process 500 associated with utilizing a machine learning model to adjust CBCT device trajectories for artifact avoidance. In some implementations, one or more process blocks of FIG. 5 may be performed by a device (e.g., surgical system 301). In some implementations, one or more process blocks of FIG. 5 may be performed by another device or a group of devices separate from or including the device, such as a CBCT device (e.g., CBCT device 330). Additionally, or alternatively, one or more process blocks of FIG. 5 may be performed by one or more components of device 400, such as processor 420, memory 430, storage component 440, input component 450, output component 460, communication component 470, and/or the like.

As shown in FIG. 5, process 500 may include receiving an X-ray image captured by a C-arm CBCT device at a particular position defined by a six-degree of freedom pose relative to an anatomy (block 510). For example, the device may receive an X-ray image captured by a C-arm CBCT device at a particular position defined by a six-degree of freedom pose relative to an anatomy, as described above.

As further shown in FIG. 5, process 500 may include processing the X-ray image, with a machine learning model, to determine a predicted quality of next possible X-ray images provided by the C-arm CBCT device (block 520). For example, the device may process the X-ray image, with a machine learning model, to determine a predicted quality of next possible X-ray images provided by the C-arm CBCT device, as described above.

As further shown in FIG. 5, process 500 may include utilizing the machine learning model to identify a particular X-ray image, of the next possible X-ray images, with a greatest predicted quality, and update the six-degree of freedom pose based on the particular X-ray image and to generate an updated six-degree of freedom pose (block 530). For example, the device may utilize the machine learning model to identify a particular X-ray image, of the next possible X-ray images, with a greatest predicted quality, and update the six-degree of freedom pose based on the particular X-ray image and to generate an updated six-degree of freedom pose, as described above.

As further shown in FIG. 5, processing may include providing, to the C-arm CBCT device, data that identifies the updated six-degree of freedom pose, wherein the data that identifies the updated six-degree of freedom pose cause the C-arm CBCT device to adjust to a new position based on the updated six-degree of freedom pose (block 540). For example, the device may provide, to the C-arm CBCT device, data that identifies the updated six-degree of freedom pose, as described above. In some implementations, the data that identifies the updated six-degree of freedom pose cause the C-arm CBCT device to adjust to a new position based on the updated six-degree of freedom pose.

Process 500 may include additional implementations, such as any single implementation or any combination of implementations described below and/or in connection with one or more other processes described elsewhere herein.

In a first implementation, the data that identifies the updated six-degree of freedom pose cause the C-arm CBCT device to acquire a new X-ray image at the new position.

In a second implementation, the X-ray image is captured by the C-arm CBCT device to verify screw placement in a spine of a patient during spinal fusion surgery.

In a third implementation, the six-degree of freedom pose includes an in-plane angle that is defined according to a circular trajectory where a source and a detector of the C-arm CBCT device move in a plane for an entire scan, and an out-of-plane angle that is associated with tilting a C-arm, of the C-arm CBCT device, relative to the plane.

In a fourth implementation, the machine learning model includes a visual geometry group (VGG) convolutional neural network model.

In a fifth implementation, processing the X-ray image, with the machine learning model, to determine the predicted quality of the next possible X-ray images provided by the C-arm CBCT device includes regressing a detectability index for the next possible X-ray images to determine the predicted quality of the next possible X-ray images.

In a sixth implementation, regressing the detectability index for the next possible X-ray images to determine the predicted quality of the next possible X-ray images includes determining a local modulation transfer function based on the X-ray image, determining a local noise power spectrum based on the X-ray image, determining a task function describing properties of an object, provided in the X-ray image, with a quality in Fourier space, and regressing the detectability index for the next possible X-ray images to determine the predicted quality of the next possible X-ray images based on the local modulation transfer function, the local noise power spectrum, and the task function.

In a seventh implementation, the machine learning model includes a convolutional neural network model adapted to perform regression instead of classification.

In an eighth implementation, the updated six-degree of freedom pose may include an updated in-plane angle that is approximately five degrees greater that an in-plane angle, and an updated out-of-plane angle that is in a range of approximately twenty-five degrees less than an out-of-plane angle to approximately twenty-five degrees greater than the out-of-plane angle.

In a ninth implementation, process 500 includes training the machine learning model based on a first dataset and a second dataset, and prior to receiving the X-ray image, wherein the first dataset is based on historical human chest CT images, and wherein the second dataset is based on a semi-anthropomorphic representation of a human chest.

In a tenth implementation, process 500 includes utilizing a synthetic dataset to test the machine learning model prior to receiving the X-ray image, utilizing a real dataset to train the machine learning model prior to receiving the X-ray image, and utilizing batch normalization and data augmentation with the machine learning model prior to receiving the X-ray image.

In an eleventh implementation, the data that identifies the updated six-degree of freedom pose reduces artifacts in future X-ray images captured by the C-arm CBCT device.

In a twelfth implementation, process 500 includes identifying a problem with a spinal fusion surgery based on one or more of the X-ray image or the next possible X-ray images, and providing a notification that identifies the problem.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method comprising:
   receiving, by a surgical system, an X-ray image captured by a device at a particular position defined by a six-degree of freedom pose relative to an anatomy;
   processing, by the surgical system, the X-ray image to determine a predicted quality of next possible X-ray images provided by the device;

identifying, by the surgical system, a particular X-ray image, of the next possible X-ray images, with a greatest predicted quality;

updating, by the surgical system, the six-degree of freedom pose based on the particular X-ray image and to generate an updated six-degree of freedom pose; and causing, by the surgical system, the device to adjust to a new position based on the updated six-degree of freedom pose.

2. The method of claim 1, further comprising:

receiving a next X-ray image captured by the device at a new position defined by the updated six-degree of freedom pose, wherein the next X-ray image corresponds to the particular X-ray image.

3. The method of claim 1, wherein the X-ray image is captured by the device to verify screw placement in a spine of a patient during spinal fusion surgery.

4. The method of claim 1, wherein the six-degree of freedom pose comprises an in-plane angle and an out-of-plane angle associated with a C-arm of the device.

5. The method of claim 4, wherein the in-plane angle is defined according to a circular trajectory where a source and a detector of the device move in a plane for an entire scan, and wherein the out-of-plane angle is associated with tilting a C-arm, of the device, relative to the plane.

6. The method of claim 1, wherein processing the X-ray image to determine the predicted quality of the next possible X-ray images provided by the device comprises:

regressing a detectability index for the next possible X-ray images to determine the predicted quality of the next possible X-ray images.

7. The method of claim 6, wherein regressing the detectability index for the next possible X-ray images to determine the predicted quality of the next possible X-ray images comprises:

determining a local modulation transfer function based on the X-ray image;

determining a local noise power spectrum based on the X-ray image;

determining a task function describing properties of an object, provided in the X-ray image, with a quality in Fourier space; and regressing the detectability index for the next possible X-ray images to determine the predicted quality of the next possible X-ray images based on the local modulation transfer function, the local noise power spectrum, and the task function.

8. A surgical system comprising:

one or more memories; and one or more processors, communicatively coupled to the one or more memories, configured to:

receive an X-ray image captured by a device at a particular position defined by a six-degree of freedom pose relative to an anatomy;

process the X-ray image to determine a predicted quality of next possible X-ray images provided by the device;

identify a particular X-ray image, of the next possible X-ray images, with a greatest predicted quality;

update the six-degree of freedom pose based on the particular X-ray image and to generate an updated six-degree of freedom pose; and cause the device to adjust to a new position based on the updated six-degree of freedom pose.

9. The surgical system of claim 8, wherein the one or more processors are further configured to:

receive a next X-ray image captured by the device at a new position defined by the updated six-degree of freedom pose, wherein the next X-ray image corresponds to the particular X-ray image.

10. The surgical system of claim 8, wherein the X-ray image is captured by the device to verify screw placement in a spine of a patient during spinal fusion surgery.

11. The surgical system of claim 8, wherein the six-degree of freedom pose comprises an in-plane angle and an out-of-plane angle associated with a C-arm of the device.

12. The surgical system of claim 11, wherein the in-plane angle is defined according to a circular trajectory where a source and a detector of the device move in a plane for an entire scan, and wherein the out-of-plane angle is associated with tilting a C-arm, of the device, relative to the plane.

13. The surgical system of claim 8, wherein the one or more processors, to process the X-ray image to determine the predicted quality of the next possible X-ray images provided by the device, are configured to:

regress a detectability index for the next possible X-ray images to determine the predicted quality of the next possible X-ray images.

14. The surgical system of claim 13, wherein the one or more processors, to regress the detectability index for the next possible X-ray images to determine the predicted quality of the next possible X-ray images, are configured to:

determine a local modulation transfer function based on the X-ray image;

determine a local noise power spectrum based on the X-ray image;

determine a task function describing properties of an object, provided in the X-ray image, with a quality in Fourier space; and regress the detectability index for the next possible X-ray images to determine the predicted quality of the next possible X-ray images based on the local modulation transfer function, the local noise power spectrum, and the task function.

15. A non-transitory computer-readable medium storing a set of instructions, the set of instructions comprising:

one or more instructions that, when executed by one or more processors of a surgical system, cause the surgical system to:

receive an X-ray image captured by a device at a particular position defined by a six-degree of freedom pose relative to an anatomy;

process the X-ray image to determine a predicted quality of next possible X-ray images provided by the device;

identify a particular X-ray image, of the next possible X-ray images, with a greatest predicted quality;

update the six-degree of freedom pose based on the particular X-ray image and to generate an updated six-degree of freedom pose; and cause the device to adjust to a new position based on the updated six-degree of freedom pose.

16. The non-transitory computer-readable medium of claim 15, wherein the one or more instructions, when executed by one or more processors of the surgical system, further cause the surgical system:

receive a next X-ray image captured by the device at a new position defined by the updated six-degree of freedom pose, wherein the next X-ray image corresponds to the particular X-ray image.

17. The non-transitory computer-readable medium of claim 15, wherein the X-ray image is captured by the device to verify screw placement in a spine of a patient during spinal fusion surgery.

18. The non-transitory computer-readable medium of claim 15, wherein the six-degree of freedom pose comprises an in-plane angle and an out-of-plane angle associated with a C-arm of the device.

19. The non-transitory computer-readable medium of claim 18, wherein the in-plane angle is defined according to a circular trajectory where a source and a detector of the device move in a plane for an entire scan, and
 wherein the out-of-plane angle is associated with tilting a C-arm, of the device, relative to the plane.

20. The non-transitory computer-readable medium of claim 15, wherein the one or more instructions, that cause the surgical system to process the X-ray image to determine the predicted quality of the next possible X-ray images provided by the device, cause the surgical system to:
 determine a local modulation transfer function based on the X-ray image;
 determine a local noise power spectrum based on the X-ray image;
 determine a task function describing properties of an object, provided in the X-ray image, with a quality in Fourier space; and
 regress a detectability index for the next possible X-ray images to determine the predicted quality of the next possible X-ray images based on the local modulation transfer function, the local noise power spectrum, and the task function.

* * * * *